United States Patent
Merade et al.

(10) Patent No.: US 7,393,319 B2
(45) Date of Patent: Jul. 1, 2008

(54) IMPLANTABLE SLING HAVING BLADDER SUPPORT

(75) Inventors: Bryon Merade, Thousand Oaks, CA (US); Red Alinsod, Glendale, CA (US)

(73) Assignee: Caldera Medical, Inc., Agoura Hills, CA (US)

( * ) Notice: Subject to any disclaimer, the term of this patent is extended or adjusted under 35 U.S.C. 154(b) by 0 days.

(21) Appl. No.: 10/684,861

(22) Filed: Oct. 14, 2003

(65) Prior Publication Data
US 2005/0080317 A1  Apr. 14, 2005

(51) Int. Cl.
*A61F 2/00* (2006.01)
(52) U.S. Cl. .......................... 600/30; 600/37
(58) Field of Classification Search ............. 600/29–31, 600/37; 128/DIG. 25, 885, 887; 606/151–158
See application file for complete search history.

(56) References Cited

U.S. PATENT DOCUMENTS

| | | | |
|---|---|---|---|
| 5,934,283 A * | 8/1999 | Willem et al. ............... | 128/885 |
| 6,050,937 A | 4/2000 | Benderev | |
| 6,197,036 B1 * | 3/2001 | Tripp et al. .................. | 606/151 |
| 6,200,330 B1 | 3/2001 | Benderev | |
| 6,302,840 B1 | 10/2001 | Benderev | |
| 6,592,515 B2 * | 7/2003 | Thierfelder et al. ............ | 600/37 |
| 6,666,817 B2 * | 12/2003 | Li ................................ | 600/30 |
| 2004/0039453 A1 | 2/2004 | Anderson et al. | |
| 2004/0144395 A1 * | 7/2004 | Evans et al. ................. | 128/885 |
| 2005/0004427 A1 | 1/2005 | Cervigni | |

OTHER PUBLICATIONS

Chon, J.; D. Bodell, K. Kobashi, G. Leach; Results of the Transvaginal Cadaveric Prolapse Repair with Sling (CAPS); p. 150, 2002.
Kobashi, K.; The use of Solvent-Dehydrated Cadaveric Fascia Lata (Tutoplast) in Slings and Cystocele Repairs: The Virginia Mason Experience: Virginia Mason Medical Center; p. 151, 2002.
Almeida, Silvio H.M., et al.; Use of Cadaveric Fascia Lata to Correct Grade IV Cystocele; Official Journal of the Brazilian Society of Urology, State University of Londrian, Parana, Brazil; p. 48-52, 2003.
Kobashi, K., S. Mee, G. Leach; A New Technique for Cystocele Repair and Transvaginal Sling: The Cadaveric Prolapse Repair and Sling (CaPS); Elsevier Science Inc.; Dec. 2000; pp. 9-14.

* cited by examiner

*Primary Examiner*—John P. Lacyk
(74) *Attorney, Agent, or Firm*—Inskeep IP Group, Inc.

(57) ABSTRACT

Surgical implants operative to simultaneously function as a pubovaginal sling for the treatment of incontinence and as a support member to effectuate cystocele repair. The implant comprises a first sling portion operative to be positioned beneath the urethra, per conventional pubovaginal sling surgery. The implant further includes a second bladder support portion extending from the sling support portion that is oriented to extend beneath and be surgically attached to a portion of the bladder to thus enable the same to be supported to a degree necessary to effectuate cystocele repair. The implant may be fabricated from a unitary piece of harvested tissue, synthetic material or combinations thereof. Preferably, the sling portion of the implant is fabricated from a synthetic material whereas the bladder support portion of the implant comprises a segment of harvested tissue sewn to the sling portion.

31 Claims, 1 Drawing Sheet

IMPLANTABLE SLING HAVING BLADDER SUPPORT

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

Concomitant cystocele repair and placement of a pubovaginal sling for the treatment of urinary incontinence by means of a transvaginal approach is known in the art. In this regard, a high correlation exists between such medical conditions and it is frequently desirable to address both via a single surgical procedure. Specifically, such procedure seeks to accomplish both goals of lifting and tightening the tissue around the bladder so that it no longer pushes against weakened tissue in the front wall of the vagina (i.e., cystocele) and positioning a sling beneath the urethra in order to provide structural support thereto such that accidental leakage of urine is eliminated or substantially reduced, particularly during provocative events such as coughing and the like.

The specifics regarding suburethral sling surgical procedures are described in detail in the references of Blaivas, Jerry G., Successful Pubovaginal Sling Surgery, Contemporary Urology, July, 1993; Blaivas, Jerry, G. Treatment of Female Incontinence Secondary To Urethral Damage Or Loss, Urologic Clinics of North America, Vol. 18, No. 2, May, 1991; Raz, Schlomo, Surgical Therapy For Urinary Incontinence, Atlas Of Transvaginal Surgery, W. B. Saunders, 1992, Loughlin, K. R., The Endoscopic Fascial Sling Treatment of Female Urinary Stress Incontinence, J. Urol, 1996, A.P.R.; 155 (4): 1265-7; and Staskin, D. R., et al., The Gore-Tex Sling Procedure For Female Sphincteric Incontinence: Indications, Technique And Results, J. Urol, 1997; 15(5): 295-9, the teachings of which are expressly incorporated herein by reference.

With respect to the simultaneous repair of the cystocele and placement of a pubovaginal sling, such procedure is disclosed by Kobashi et al., in the reference *A New Technique for Cystocele Repair and Transvaginal Sling: the Cadaveric Prolapse Repair and Sling (CaPS)*, Urology, December, 2000 4:56 (Suppl. 1): 9-14 and by Chung et al., in the reference *Technique of Combined Pubovaginal Sling and Cystocele Repair Using a Single Piece of Cadaveric Dermal Graft*, Urology. 2002 April; 59(4): 538-41, the teachings of each of which are expressly incorporated herein by reference.

Despite the optimal opportunity to concurrently perform cystocele repair and pubovaginal sling surgery via a transvaginal approach, there has not to date been any type of implantable support material/tissue that is readily sized and configured to be surgically affixed into position such that both the bladder is properly supported (i.e., so that it no longer pushes against the vagina), and that the urethra is provided with a suburethral sling optimally positioned to treat the related condition of incontinence. In this respect, to the extent concurrent cystocele repair and pubovaginal sling surgery are performed, the prior art teaches the use of a harvested piece of tissue derived from a cadaver that must be surgically fashioned for implantation within a particular patient. To derive such implantable material, however, is exceptionally problematic due to the requirement that cadaveric tissue be available. Moreover, even to the extent a source of cadaveric tissue is available, the same must necessarily be excised to near precise dimensions and thereafter implanted with great care. In this respect, to the extent the harvested tissue is improperly sized or is otherwise torn or damaged during implantation, such supportive material will be rendered useless and require that at least one additional segment of material be harvested. As a consequence, substantial time, expense, and potential patient discomfort associated with such surgical procedure can frequently occur.

Accordingly, there is a substantial need in the art for a surgical implant operative to serve both as a suburethral sling for the treatment of incontinence, as well as provide structural support necessary to effectuate cystocele repair. There is additionally a need in the art for such an implant that can be readily fabricated from known implantable materials, and specifically sized and configured for immediate surgical implantation in procedures involving both the placement of a suburethral sling and supportive tissue to effectuate cystocele repair. There is still a further need in the art for such an implant that may be fabricated from materials possessing desirable properties, such as biocompatibility, material strength, and adaptability for use in surgical procedures. There is yet a further need in the art for such an implant that is of exceedingly simple construction, low cost to manufacture, and is capable of being readily deployed using known surgical techniques.

BRIEF SUMMARY OF THE INVENTION

The present invention specifically addresses and alleviates the above-identified deficiencies in the art. In this regard, the present invention is direct to an implant operative to simultaneously function as a suburethral sling for the treatment of incontinence, as well as provide lift and support about the bladder so that it no longer pushes against the vagina and thus effectuate cystocele repair. According to a preferred embodiment, the implant comprises a first sling portion sized and configured as per conventional suburethral slings for positioning and placement beneath the urethra to provide a sufficient degree of urethral support. Such implant includes a second bladder support portion affixed to or formed as part of the sling portion that is operative to be surgically interconnected about a portion of the bladder to enable the latter to be lifted and supported to a degree necessary to effectuate cystocele repair. Preferably, the implant will possess a generally T-shape with the first sling portion defining an elongate strip having opposed ends, a front portion and a rear portion. The second implant portion will be affixed medially about a portion of the rear peripheral edge of the first sling portion and extend rearwardly therefrom. The implant may be fabricated such that both sling and bladder support portions are integrally formed from a single piece of harvested tissue. Alternatively, the sling and bladder support portions will be integrally formed from a unitary piece of synthetic material. Still further, the implant may be fabricated such that a respective one of the sling portion or bladder support portion is fabricated from a synthetic material with the respective other portion being fabricated from a piece of harvested tissue and coupled to the respective other piece via stitching or any other means known in the art to couple the two implant portions to one another. In a most highly preferred embodiment, the sling portion of the implant will be comprised from a synthetic material, which may be selected from a variety of well-known materials in the art, and the bladder support portion will comprise a graft harvested from a donor, which may comprise a cadaver, another human subject, an animal, such as a pig, and even the patient herself.

Advantageously, by providing a pre-formed implant operative to provide both suburethral support concomitantly with the bladder support necessary to perform cystocele repair, both conditions (i.e., incontinence and cystocele) can be treated via a single surgical procedure. Moreover, by providing a readily-fabricated implant, there is thus eliminated the need to surgically fashion such a support from cadaverous tissue, thus tremendously reducing the time necessary to perform such procedure, as well as eliminating the need to have a source of cadaverous tissue available. Furthermore, in those embodiments where the implant is comprised of a sling portion fabricated from a synthetic material and a bladder support portion formed from a graft or harvested tissue, such embodiment allows for rapid fabrication that further enables the implant to possess exceptional durability with respect to the sling component thereof and optimal biocompatibility with respect to the bladder support portion thereof.

With respect to the surgical implantation of the implants of the present invention, the same may be deployed through any known procedure in the art. Along these lines, such implant may be secured in position pursuant to those procedures disclosed by Kobashi et al., in the reference *A New Technique for Cystocele Repair and Transvaginal Sling: the Cadaveric Prolapse Repair and Sling*, referred to above.

It is therefore an object of the present invention to provide an implantable sling having bladder support that enables pubovaginal sling surgery and cystocele repair to be performed via a single surgical procedure.

Another object of the present invention is to provide an implantable sling having bladder support that enables pubovaginal sling surgery and cystocele repair to be performed in a manner that eliminates the need to surgically fashion an implant operative to simultaneously impart suburethral support for the treatment of incontinence and also impart a sufficient degree of support to the bladder to effectuate cystocele repair.

Another object of the present invention is to provide an implantable sling having bladder support that enables pubovaginal sling surgery and cystocele repair to be performed in a manner that eliminates any dependency on a readily accessible source of cadaverous tissue during such surgical procedure.

Another object of the present invention is to provide an implantable sling having bladder support that may be easily and readily fabricated from known implantable materials, is of simple construction, is easy to surgically manipulate, is exceptional durable in functioning as an implant, and is of relatively low cost.

Still further objects of the present invention are to provide methods for using the implants of the present invention to thus simultaneously effectuate cystocele repair and urinary incontinence that is substantially more time efficient, easier to perform, and more cost effective than prior art techniques.

BRIEF DESCRIPTION OF THE DRAWINGS

These as well as other features of the present invention will become more apparent upon reference to the drawings

DETAILED DESCRIPTION OF THE INVENTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figure 1:
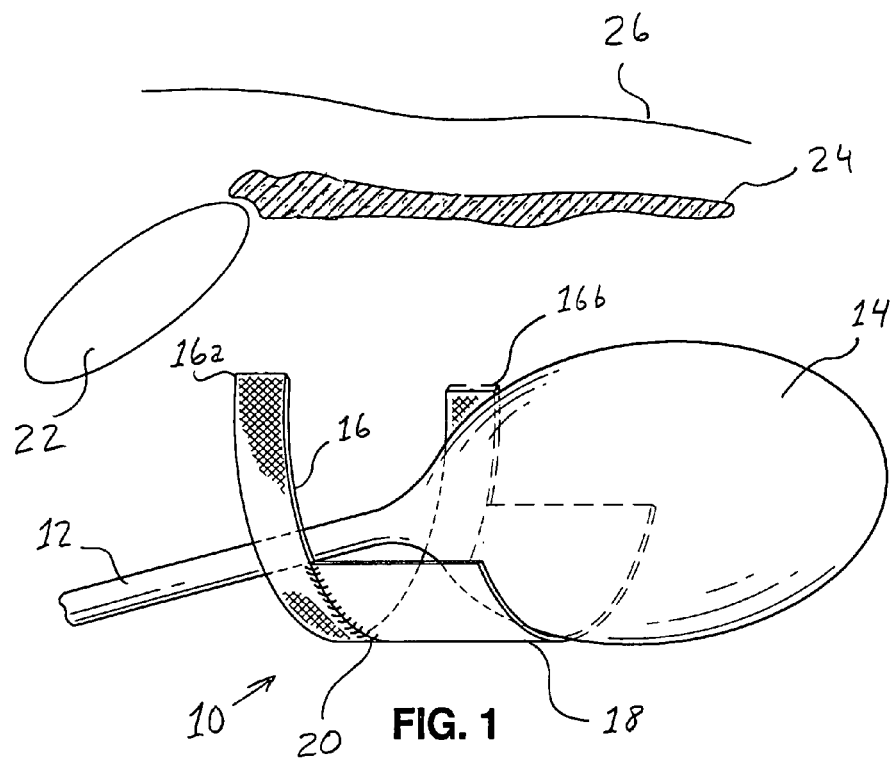
FIG. 1 is a perspective view of an implant comprised of a suburethral sling having a bladder support portion for use in performing cystocele repair.

Referring now to the Figures, and initially to FIG. 1, there is shown an implant 10 for use in concomitantly functioning as a pubovaginal sling for use in the treatment of incontinence, as well as providing support necessary to effectuate cystocele repair. In this respect, the implant 10 is operative to simultaneously impart support to the urethra 12 and a portion of the bladder 14 when implanted via a single surgical procedure. As discussed in the background, it is well-known in the art that cystocele and incontinence are frequently related conditions that, for appropriate patients, warrants that both conditions be treated, preferably via a single surgical procedure.

To that end, the implant 10 is specifically fashioned and configured to address both such conditions. According to the preferred embodiment shown, the implant 10 comprises a first sling portion 16 that is operatively positioned beneath a portion of the urethra 12. As per conventional sling procedures, the sling portion 16 is fashioned as an elongate strip having opposed ends 16a, 16b, that are secured into position via a variety of techniques well-known to those skilled in the art. In this regard, such opposed ends 16a, 16b, may be secured to the pubic bone 22, fascia 24, or other structures, such as Cooper's ligament (not shown), or any other method well-known to those skilled in the art. In this regard, it is contemplated that such methods for securing the opposed ends 16a, 16b, into position such that the sling portion 16 is positioned beneath the urethra may take any of those types of procedures described in U.S. Pat. No. 6,200,330 to Benderev, et al., entitled SYSTEMS FOR SECURING SUTURES, GRAFTS AND SOFT TISSUE TO BONE AND PERIOSTEUM, issued Mar. 13, 2001, the teachings of which are expressly incorporated herein by reference.

Alternatively, such sling portion 16 may be configured per well-known and commercially available slings currently in use, including the TVT tension-free vaginal tape produced by Johnson and Johnson of Summerville, N.J. or the SPARC sling system for curing female stress urinary incontinence produced by American Medical Systems of Minneapolis, Minn. The structure related to such commercially-available products is expressly incorporated herein by reference. In this regard, such sling systems are operatively positioned such that a portion of the sling extends beneath the urethra with the opposed free ends of the sling remaining as free ends that are not secured to any type of anatomical structure. In this respect, it is expressly contemplated that the sling portion 16 of the implant 10 of the present invention may be operatively fashioned according to such slings embodying such principles.

In addition to the sling portion 16, the implant 10 is further provided with a bladder support portion 18. As illustrated, the bladder support portion 18 is operative to extend rearwardly from a portion of the peripheral edge of the sling portion 16, and extend at least partially about the underside of bladder 14, as shown. As will be appreciated by those skilled in the art, such bladder support portion 18 will be operative to lift and support the bladder 14 to a degree sufficient to effectuate cystocele repair. In this regard, it is contemplated that bladder support portion 18 will be specifically configured and fashioned per conventional implantable tissue masses or synthetic materials utilized in cystocele repair necessary to support the bladder 14 via the introduction of such tissue portion 18 between the vagina and the bladder 14.

Figure 2:
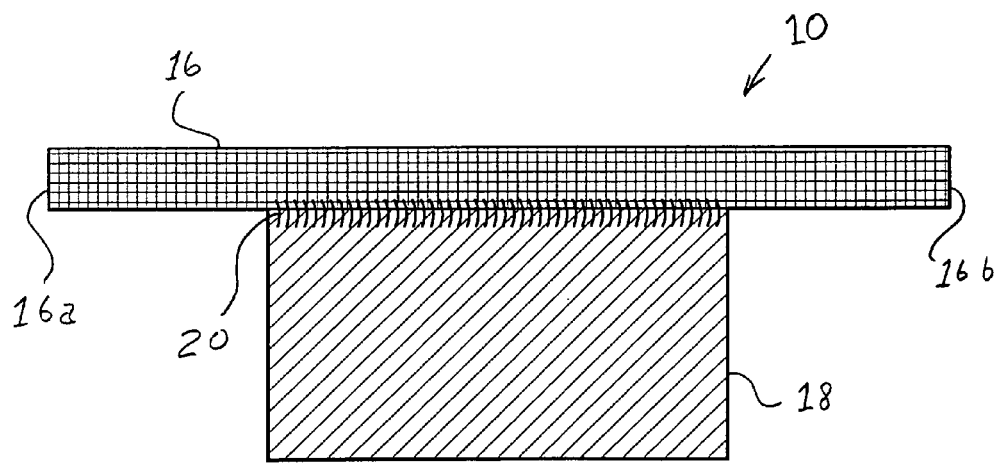
FIG. 2 is a top view of the implant depicted in FIG. 1 illustrating a first sling portion and a second bladder support portion.

In order to more clearly illustrate the construction of the implant 10 of the present invention, there is shown in FIG. 2 a frontal plan view thereof. As illustrated, the sling portion 16 will be constructed as per conventional slings having a generally elongate strip preferably formed to have a generally rectangular configuration defining opposed ends 16a, 16b and a continuous peripheral edge. Formed upon a portion of the peripheral edge defining sling portion 16 is bladder support portion 18. As illustrated, bladder support portion 18 is connected upon a portion of the rear or distal peripheral edge of the sling portion 16 generally upon the medial portion thereof. In the embodiment shown, the sling portion 16 is connected to bladder support portion 18 via stitching 20 to thus enable the two pieces to remain interconnected. As will be readily appreciated by those skilled in the art, it should be understood that the implant 10, as opposed to being fabricated from two separate portions 16, 18, may be fabricated from a unitary piece of material. Along these lines, it is contemplated that the implant 10 may be fabricated from a single piece of harvested tissue that is precut and preformed to have the configuration as shown. Alternatively, the implant 10 may be fabricated from a unitary piece of synthetic material, such as surgical mesh and the like, that defines both sling portions 16 and bladder support portion 18.

In an alternative, more highly preferred embodiment, the sling portion 16 and bladder support portion 18 will be fabricated from dissimilar materials whereby one portion is fabricated from either tissue or synthetic material and the respective other portion is formed from a dissimilar type of material. Preferably, the implant will be fabricated such that sling portion 16 is formed from a synthetic material, and thus operative to provide durable support to the urethra 12 once positioned there underneath, and the bladder support portion 18 will be fabricated from a graft or section of harvested tissue. With respect to the latter, it is well-known in the art that by utilizing tissue as a material to provide bladder support provides substantially enhanced biocompatibility and generally provides for more favorable surgical outcome. Implants constructed in accordance to the aforementioned embodiment are presently being commercialized by Caldera Medical, Inc. of Thousand Oaks, Calif.

With respect to the surgical implantation of the implants of the present invention, the same may be performed utilizing any of a variety of known techniques in the art. At the present time, however, it is expressly contemplated that the implants of the present invention will be deployed transvaginally via an incision made to the vaginal wall. By utilizing a transvaginal route, access to the urethra, for placement of the sling portion 16, as well as the site of bladder prolapse will be provided via a single surgical site. Exemplary of such surgical procedures ideally suited for the placement of the present invention include those discussed by Kobashi, et al., discussed above.

Alternatively, the implants of the present invention may be secured into position via a transobturator route via known procedures in the art. In this regard, such transobturator route likewise requires the formation of an incision in the vagina through which the implant will be positioned against the urethra and bladder, respectively. To achieve that end, it is contemplated that the opposed ends of the sling portion 16 will be disposed within the obturator foramen and either secured thereto via a conventional anchoring means or otherwise remain as non-attached free ends suspended therein. As should be appreciated by those skilled in the art, however, although a transvaginal deployment is considered most ideally suited as the preferred route for surgically implanting the implants of the present invention, any type of procedure by which the bladder and the urethra can be accessed in order to surgically position the implants of the present invention should be deemed to fall within the scope of the present invention. Along these lines, it is contemplated that although possibly less efficient, the implants of the present invention may be implanted via an alternative route, such as through an incision made in the patient's abdomen (i.e., suprapubic route), the top surface of which being depicted as 26 in FIG. 1. Accordingly, all known surgical procedures capable of deploying the implants of the present invention should be deemed to fall within the scope of the present invention.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention. Along these lines, it is expressly contemplated that the sling portion 16 may be fabricated to have any dimensions that are operative to enable the same to adequately support the urethra, as well as be adequately secured into position. Likewise, the bladder support portion may be fabricated to have any shape or dimensions that may be necessary to impart the degree of support necessary to effectuate cystocele repair. Still further, it is contemplated that the implants of the present invention can readily be utilized in related surgical procedures, such as rectocele and enterocele repair, through surgical techniques that will be readily known to those skilled in the art. In such applications, it will be readily understood that the bladder support portion 18 will be utilized to provide support to the source of herniation and, where appropriate, may be sized and configured to specifically support a target organ or tissue mass sought to be supported while at the same time providing suburethral sling support via sling portion 16. Accordingly, although depicted as generally rectangular portions, the sling portion and bladder support portion may have alternative shapes and configurations that will be readily understood by those skilled in the art.

What is claimed is:

1. A prefabricated implant for concomitantly treating incontinence and effectuating cystocele repair in a female patient in need thereof comprising:
   a. a sling portion fabricated from a first material selected for a property particularly well suited for support of a urethra, said sling portion being operatively positionable beneath the urethra of said patient; and
   b. a bladder support portion fabricated from a second material selected for a property particularly well suited for support of a bladder, said bladder support portion being operatively positionable to substantially prevent said bladder from pushing against the vagina of said patient; and,
   c. said bladder support portion connected to and extending from said sling portion; and,
   d. said property particularly well suited for support of a urethra being absent in said second material and said property particularly well suited for support of a bladder being absent in said first material.

2. The implant of claim 1, wherein said sling portion comprises an elongate segment defining opposed ends.

3. The implant of claim 2, wherein said sling portion has a generally rectangular shape.

4. The implant of claim 1, wherein said sling portion and said bladder support portion are integrally formed with one another.

5. The implant of claim 4, wherein said first material is a synthetic.

6. The implant of claim 1, wherein said sling portion defines a continuous peripheral edge and said bladder support portion defines a continuous peripheral edge, said sling portion and said bladder support portion being interconnected to one another by a segment of stitching whereby a portion of said peripheral edge of said sling portion is stitched to a portion of said peripheral edge of said bladder support portion.

7. The implant of claim 6, wherein said second material is harvested tissue and said first material is synthetic material.

8. The implant of claim 6, wherein said sling portion and said bladder support portion cooperate to define a generally T-shape.

9. A method for concomitantly treating a female patient afflicted with urinary incontinence and effectuating cystocele repair via a single surgical procedure comprising the steps:
   a. providing a pre-fabricated implant comprising:
      i. a sling portion selected for a property particularly well suited for support of a urethra, said sling portion being operatively positionable beneath the urethra of said patient; and
      ii. a bladder support portion selected for a property particularly well suited for support of a bladder, said bladder support portion formed from harvested tissue and connected to and extending from said sling portion, said bladder support portion being operatively positionable against said bladder of said patient to substantially prevent said bladder from pushing against the vagina of said patient, said property particularly well suited for support of a urethra being absent in said bladder support portion and said property particularly well suited for support of a bladder being absent in said sling portion;
   b. forming an incision within the vagina of said patient; and
   c. transvaginally implanting said implant provided in step (a) through said incision made in step (b) such that said sling portion of said implant is operatively positioned beneath the urethra of said patient and said bladder support portion of said implant is operatively positioned to substantially prevent said bladder from pushing against the vagina.

10. A method for concomitantly treating a female patient afflicted with urinary incontinence and effectuating cystocele repair via a single surgical procedure comprising the steps:
    a. providing a pre-fabricated implant comprising:
       i. a sling portion selected for a property particularly well suited for support of a urethra, said sling portion being operatively positionable beneath the urethra of said patient; and
       ii. a bladder support portion selected for a property particularly well suited for support of a bladder, said bladder support portion connected to and extending from said sling portion, said bladder support portion being operatively positionable to substantially prevent said bladder from pushing against the vagina of said patient, said property particularly well suited for support of a urethra being absent in said bladder support portion and said property particularly well suited for support of a bladder being absent in said sling portion;
    b. forming an incision within the abdomen of said patient; and
    c. implanting said implant provided in step (a) through said incision made in step (b) such that said sling portion of said implant is operatively positioned beneath the urethra of said patient and said bladder support portion of said implant is operatively positioned to substantially prevent said bladder from pushing against the vagina.

11. A method for concomitantly treating a female patient afflicted with urinary incontinence and effectuating cystocele repair via a single surgical procedure comprising the steps:
    a. providing a prefabricated implant comprising:
       i. a sling portion selected for a property particularly well suited for support of a urethra, said sling portion being operatively positionable beneath the urethra of said patient; and
       ii. a bladder support portion selected for a property particularly well suited for support of a bladder, said bladder support portion connected to and extending from said sling portion, said bladder support portion being operatively positionable to substantially prevent said bladder from pushing against the vagina of said patient, said property particularly well suited for support of a urethra being absent in said bladder support portion and said property particularly well suited for support of a bladder being absent in said sling portion;
    b. forming at least one incision in said patient; and
    c. implanting said implant provided in step (a) and into the obturator foramen via said at least one incision made in step (b) such that said sling portion of said implant is operatively positioned beneath the urethra of said patient and said bladder support portion of said implant is operatively positioned to substantially prevent said bladder from pushing against the vagina.

12. An implant for concomitantly treating incontinence and effectuating rectocele repair in a patient in need thereof comprising:
    a. a sling portion fabricated from a first material selected for a property particularly well suited for support of a urethra, said sling portion being operatively positionable beneath the urethra of said patient; and
    b. a rectum support portion fabricated from a second material selected for a property particularly well suited for support of a rectum said rectum support portion being operatively positionable to substantially eliminate prolapse of the rectum; and,
    c. said rectum support portion connected to and extending from said sling portion; and,
    d. said property particularly well suited for support of a urethra being absent in said second material and said property particularly well suited for support of a rectum being absent in said first material.

13. An implant for concomitantly treating incontinence and effectuating enterocele repair in a patient in need thereof comprising:
    a. a sling portion fabricated from a first material selected for a property particularly well suited for support of a urethra, said sling portion being operatively positionable beneath the urethra of said patient; and
    b. an intestinal support portion fabricated from a second material selected for a property particularly well suited for support of an intestine, said intestinal support portion being operatively positionable to effectuate enterocele repair; and,
    c. said intestinal support portion connected to and extending from said sling portion; and, d. said property particularly well suited for support of a urethra being absent in said second material and said property particularly well suited for support of an intestine being absent in said first material.

14. The implant of claim 6, wherein said second material is harvested tissue.

15. The implant of claim 6, wherein said first material is synthetic.

16. A method for concomitantly treating a female patient afflicted with urinary incontinence and effectuating rectocele repair via a single surgical procedure comprising the steps:
   a. providing a pre-fabricated implant comprising:
      i. a sling portion formed from a first material selected for a property particularly well suited for support of a urethra, said sling portion being operatively positionable beneath the urethra of said patient; and
      ii. a rectum support portion formed from a second material selected for a property particularly well suited for support of a rectum and connected to and extending from said sling portion, said rectum support portion being operatively positionable to substantially prevent said rectum from pushing against the vagina of said patient;
      iii. said rectum support portion connected to and extending from said sling portion; and,
      iv. said property particularly well suited for support of a urethra being absent in said second material and said property particularly well suited for support of a rectum being absent in said first material
   b. forming an incision within said patient; and
   c. implanting said implant provided in step (a) through said incision made in step (b) such that said sling portion of said implant is operatively positioned beneath the urethra of said patient and said rectum support portion of said implant is operatively positioned to substantially prevent said rectum from pushing against the vagina.

17. The method of claim 16, wherein in step (b), said incision is made within the vagina of said patient.

18. The method of claim 16, wherein in step (a), said implant is fabricated from a material selected from the group consisting of a synthetic material and a harvested tissue.

19. The method of claim 18 wherein in step (a), said sling portion of said implant is fabricated from a synthetic material and said rectum support portion is fabricated from harvested tissue.

20. A method for concomitantly treating a female patient afflicted with urinary incontinence and effectuating enterocele repair via a single surgical procedure comprising the steps:
   a. providing a pre-fabricated implant comprising:
      i. a sling portion formed from a first material selected for a property particularly well suited for support of a urethra, said sling portion being operatively positionable beneath the urethra of said patient; and
      ii. an intestinal support portion formed from a second material selected for a property particularly well suited for support of an intestine, said intestinal support portion being operatively positionable to substantially prevent said intestine from pushing against the vagina of said patient;
      iii. said intestinal support portion connected to and extending from said sling portion; and,
      iv. said property particularly well suited for support of a urethra being absent in said second material and said property particularly well suited for support of an intestine being absent in said first material
   b. forming an incision within said patient; and
   c. implanting said implant provided in step (a) through said incision made in step (b) such that said sling portion of said implant is operatively positioned beneath the urethra of said patient and said intestinal support portion of said implant is operatively positioned to substantially prevent said intestine from pushing against the vagina.

21. The method of claim 20, wherein in step (b), said incision is made within the vagina of said patient.

22. The method of claim 20, wherein in step (a), said implant is fabricated from a material selected from the group consisting of a synthetic material and a harvested tissue.

23. The method of claim 22, wherein in step (a), said sling portion of said implant is fabricated from a synthetic material and said intestinal support portion is fabricated from harvested tissue.

24. The prefabricated implant according to claim 1, wherein said property particularly well suited for support of a urethra is exceptional durability and said property particularly well suited for support of a bladder is optimal biocompatibility.

25. The method of claim 9, wherein in step (a), said property particularly well suited for support of a urethra is exceptional durability and said property particularly well suited for support of a bladder is optimal biocompatibility.

26. The method of claim 10, wherein in step (a), said property particularly well suited for support of a urethra is exceptional durability and said property particularly well suited for support of a bladder is optimal biocompatibility.

27. The method of claim 11, wherein in step (a), said property particularly well suited for support of a urethra is exceptional durability and said property particularly well suited for support of a bladder is optimal biocompatibility.

28. The implant according to claim 12, wherein said property particularly well suited for support of a urethra is exceptional durability and said property particularly well suited for support of a rectum is optimal biocompatibility.

29. The implant according to claim 13, wherein said property particularly well suited for support of a urethra is exceptional durability and said property particularly well suited for support of an intestine is optimal biocompatibility.

30. The method of claim 16, wherein in step (a), said property particularly well suited for support of a urethra is exceptional durability and said property particularly well suited for support of a rectum is optimal biocompatibility.

31. The method of claim 20, wherein in step (a), said property particularly well suited for support of a urethra is exceptional durability and said property particularly well suited for support of an intestine is optimal biocompatibility.

* * * * *